(12) United States Patent
Chen et al.

(10) Patent No.: US 10,888,299 B2
(45) Date of Patent: Jan. 12, 2021

(54) METHOD AND APPARATUS FOR X-RAY IMAGING AND GAIN CALIBRATION OF DETECTOR AND DETECTOR BRACKET

(71) Applicant: GENERAL ELECTRIC COMPANY, Schenectady, NY (US)

(72) Inventors: Peijun Chen, Beijing (CN); Wei Zhao, Beijing (CN); Yongtao Tan, Beijing (CN); Rowland Saunders, Hartland, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 908 days.

(21) Appl. No.: 15/360,622

(22) Filed: Nov. 23, 2016

(65) Prior Publication Data
US 2017/0181724 A1    Jun. 29, 2017

(30) Foreign Application Priority Data

Dec. 29, 2015    (CN) .......................... 2015 1 1016179

(51) Int. Cl.
| | | |
|---|---|---|
| *A61B 6/00* | (2006.01) | |
| *H04N 5/52* | (2006.01) | |
| *A61B 5/00* | (2006.01) | |
| *H04N 5/367* | (2011.01) | |
| *H01L 27/146* | (2006.01) | |

(52) U.S. Cl.
CPC ............ *A61B 6/585* (2013.01); *A61B 5/7225* (2013.01); *H04N 5/52* (2013.01); *A61B 5/72* (2013.01);
(Continued)

(58) Field of Classification Search
CPC ....... A61B 5/72; A61B 5/7203; A61B 5/7221; A61B 5/7225; A61B 6/42; A61B 6/52; A61B 6/5258; A61B 6/58; A61B 6/582; A61B 6/585; A61B 6/587; A61B 6/588; A61B 2560/02; A61B 2560/0223; A61B 2560/0228; A61B 2560/0233; A61B 2560/0238; A61B 2562/04; A61B 2562/046; H01L 27/14; H01L 27/144; H01L 27/1446; H01L 27/146; H01L 27/14601; H01L 27/14658; H01L 27/14659; H01L 27/14661; H01L 27/14663; H01L 27/14676; H01L 27/148; H01L 27/14806; H01L 27/14831; H04N 5/30; H04N 5/367; H04N 5/3675; H04N 5/365; H04N 5/3651; H04N 5/3653; H04N 5/32; H04N 5/3205; H04N 5/23229; H04N 5/23232; H04N 5/235; H04N 5/243; H04N 5/2352; H04N 5/52; G06T 5/00;
(Continued)

(56) References Cited

U.S. PATENT DOCUMENTS

| | | | | |
|---|---|---|---|---|
| 6,457,861 | B1 * | 10/2002 | Petrick ................... | A61B 6/032 378/207 |
| 8,033,725 | B2 * | 10/2011 | Maack .................... | A61B 6/583 378/207 |

(Continued)

*Primary Examiner* — Anastasia Midkiff
(74) *Attorney, Agent, or Firm* — Fletcher Yoder, P.C.

(57) ABSTRACT

The present invention provides an X-ray detection device and an apparatus and method for calibrating an X-ray detector, the method for calibrating an X-ray detector comprising: retrieving a calibration parameter stored in the X-ray detector relative to the X-ray detector; and calibrating the X-ray detector according to the calibration parameter.

15 Claims, 6 Drawing Sheets

(52) U.S. Cl.
CPC ........... *A61B 6/58* (2013.01); *H01L 27/14658* (2013.01); *H04N 5/367* (2013.01)

(58) Field of Classification Search
CPC ......... G06T 5/001; G06T 5/002; G06T 5/005; G06T 5/50; G06T 7/0002; G06T 7/0004; G06T 7/001; G06T 7/0012; G06T 7/0014; G06T 11/003; G06T 11/008; G06T 2207/20221; G06T 2207/20216; G06T 2207/20224; G06T 2207/10072; G06T 2207/10081; G06T 2207/20; G06T 2207/20172; G06T 2207/20182; G06T 2207/20212
See application file for complete search history.

(56) References Cited

U.S. PATENT DOCUMENTS

| | | | | |
|---|---|---|---|---|
| 2001/0033678 A1* | 10/2001 | Hirai | ...................... | H04N 1/401 382/128 |
| 2003/0183771 A1* | 10/2003 | Hirai | ........................ | H04N 5/32 250/370.09 |
| 2004/0120468 A1* | 6/2004 | Dhawale | ................. | A61B 6/482 378/207 |
| 2005/0061963 A1* | 3/2005 | Spahn | .................... | G12B 13/00 250/252.1 |
| 2005/0092909 A1* | 5/2005 | Spahn | ................... | G01T 1/2018 250/252.1 |
| 2010/0054400 A1* | 3/2010 | Ren | ........................ | A61B 6/025 378/37 |
| 2011/0057802 A1* | 3/2011 | Topfer | ................... | A61B 6/585 340/584 |
| 2013/0114790 A1* | 5/2013 | Fabrizio | ................... | A61B 6/02 378/62 |
| 2013/0121478 A1* | 5/2013 | Hansroul | ................ | G01T 7/005 378/207 |
| 2013/0170627 A1* | 7/2013 | Topfer | ................. | A61B 6/2433 378/207 |
| 2013/0182934 A1* | 7/2013 | Topfer | ..................... | G06K 9/38 382/132 |
| 2014/0211910 A1* | 7/2014 | Subramanian | .......... | G01T 7/005 378/5 |
| 2016/0113617 A1* | 4/2016 | Herrmann | ................ | A61B 6/42 378/207 |

\* cited by examiner

METHOD AND APPARATUS FOR X-RAY IMAGING AND GAIN CALIBRATION OF DETECTOR AND DETECTOR BRACKET

FIELD OF THE INVENTION

The present invention relates to the field of medical imaging, particularly to an X-ray detection device and an apparatus and method for calibrating an X-ray detector.

BACKGROUND

When an X-ray detection device, e.g., a chest X-ray machine, a C-arm, etc. is utilized to perform X-ray medical diagnosis or treatment, an X-ray detector needs to be installed in a detection device bracket to receive an X-ray passing through a detected object and output an electric signal for image reconstruction.

As medical detection technologies are being developed, it has been realized that the same detector is applied into different X-ray detection devices to detect a lesion. However, due to pixel response non-uniformity of the X-ray detector and a bad pixel that may occur, the X-ray detector installed in the detection device bracket firstly needs to be calibrated before a patient is scanned. Otherwise, it is difficult for the acquired image of the patient to satisfy the requirements of clinical diagnosis.

The current calibration manner is comprises first irradiate the X-ray detector with the X-ray not passing through a scanned object each time after the X-ray detector is replaced in the X-ray detection device or each time after the X-ray detector is installed in a detection device bracket of another X-ray detection device, such that the X-ray detector produces an original image for calibration, a calibration parameter is then acquired based upon the original image, and the X-ray detector is calibrated according to the calibration parameter. There are also other barriers between a path of the X-ray transmitting from a bulb to the X-ray detector, which are part of the detection device bracket, e.g., a detection bed or pillar, etc. Such manner needs a relatively large workload.

Obviously, the above calibration manner needs a relatively large workload. Moreover, in a general case, a user is not allowed to perform such calibration in order to ensure the reliability of calibration. Instead, a provider will assign a professional staff to implement the calibration. As such, it is very inconvenient to use the same detector in different devices, which results in low calibration efficiency.

BRIEF SUMMARY OF THE INVENTION

One objective of the present invention is to provide an X-ray detection device and an apparatus and method for calibrating an X-ray detector, which is capable of improving calibration efficiency of the detector.

An exemplary embodiment of the present invention provides a method for calibrating an X-ray detector, comprising: retrieving a calibration parameter stored in the X-ray detector relative to the X-ray detector; and calibrating the X-ray detector according to the calibration parameter.

An exemplary embodiment of the present invention provides an apparatus for calibrating an X-ray detector, comprising a parameter acquisition module and a calibration module. The parameter acquisition module retrieves a calibration parameter stored in the X-ray detector relative to the X-ray detector, and the calibration module calibrates the X-ray detector according to the calibration parameter.

An exemplary embodiment of the present invention provides an X-ray detection device, comprising a detection device bracket and an X-ray detector installed in the detection device bracket, a calibration parameter relative to the X-ray detector being stored in the X-ray detector, the X-ray detection device further comprising processing means, the processing mean comprising the above apparatus for calibrating the X-ray detector.

Other features and aspects will be apparent through the following detailed description, figures and claims.

BRIEF DESCRIPTION OF THE DRAWINGS

The present invention can be understood better in light of the description of exemplary embodiments of the present invention with reference to the accompanying drawings, in which.

DETAILED DESCRIPTION

Hereafter, a detailed description will be given for embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
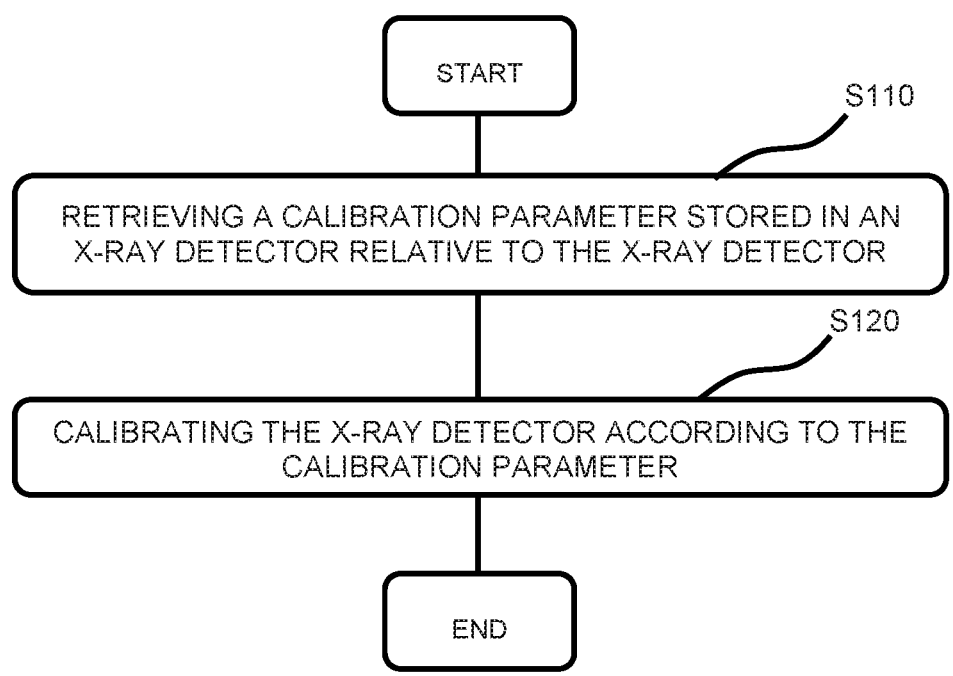
FIG. 1 is a flow chart of a method for calibrating an X-ray detector provided by an embodiment of the present invention.

FIG. 1 is a flow chart of a method for calibrating an X-ray detector provided by an embodiment of the present invention. As shown in FIG. 1, the method for calibrating an X-ray detector of the present invention includes the following steps S110 and S120.

Step S110: retrieving a calibration parameter stored in the X-ray detector relative to the X-ray detector.

Step S120: calibrating the above X-ray detector according to the above calibration parameter.

The above calibration method may be performed after the X-ray detector is installed at a detection device bracket. The above detection device bracket may include, for example, a supporting pillar of the detector, a detection bed, etc. The above X-ray detector may be a portable X-ray detector, which may be installed in the above detection device bracket and may be taken out of the detection device bracket and installed in other detection device brackets.

The above calibration parameter relative to the X-ray detector is stored in the X-ray detector. Accordingly, the calibration parameter may be directly retrieved from the X-ray detector to calibrate the detector before the patient is scanned, and it is not necessary for the detector to receive an X-ray again to produce an original image for calibration and not necessary for the detector to regenerate the calibration parameter according to the original image.

Optionally, in Step S110, "retrieving a calibration parameter stored in the X-ray detector relative to the X-ray detector" may include: retrieving a bad pixel calibration parameter stored in the X-ray detector. In other words, the above calibration parameter relative to the detector may include the bad pixel calibration parameter. In Step S120, the X-ray detector may be calibrated specifically according to the bad pixel calibration parameter.

Those skilled in the art should understand that the bad pixel calibration parameter for the X-ray detector may be: response of one or more pixels of the X-ray detector to the X-ray exceeds beyond a normal range such that an obvious highlight or black dot appears on the corresponding position of the image produced by the detector. Accordingly, positional information of the bad pixel and a calibrated X-ray response value may be included in the bad pixel calibration parameter such that the X-ray response value at the position of the bad pixel may be adjusted in Step S120.

Figure 2:
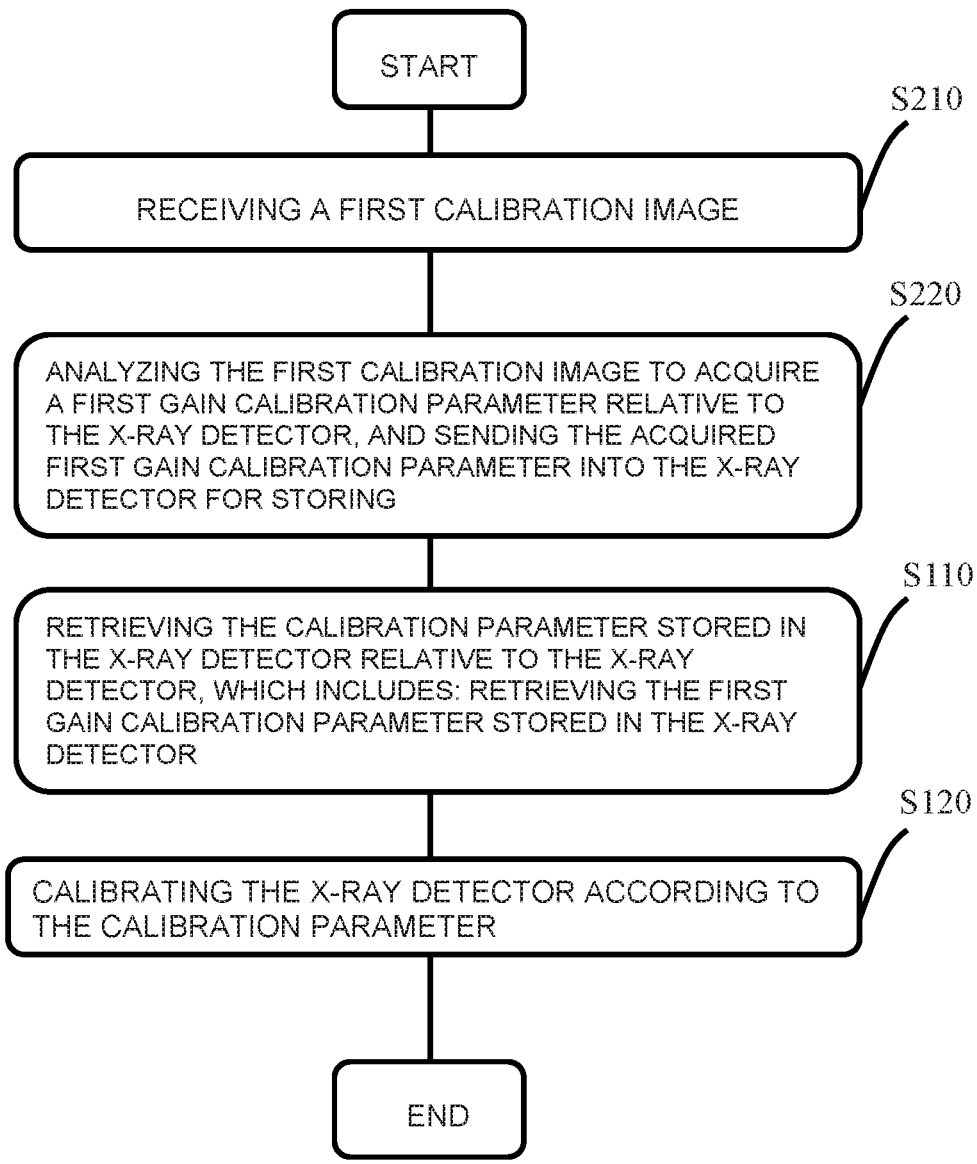
FIG. 2, is a flow chart of a method for calibrating an X-ray detector according to an embodiment of the present invention.

FIG. 2 is a flow chart of a method for calibrating an X-ray detector provided by an embodiment of the present invention. As shown in FIG. 2, the method for calibrating an X-ray detector of an embodiment is similar to the method for calibrating an X-ray detector of the FIG. 1, and the difference between the two is that: in Step S110 of FIG. 2, "retrieving a calibration parameter stored in the X-ray detector relative to the X-ray detector" may include retrieving a first gain calibration parameter stored in the X-ray detector relative to the X-ray detector, i.e., the above calibration parameter relative to the detector may include the first gain calibration parameter, and Step S120 may specifically include calibrating the X-ray detector according to the first gain calibration parameter.

Those skilled in the art should understand that the gain calibration parameter may be a parameter generated for calibrating pixel response non-uniformity of the X-ray detector. The above pixel response non-uniformity means that responses of individual pixels on the X-ray detector to the X-ray of even strength are uneven such that stripes of unequal shading appear on the corresponding positions of the original image generated by the detector, which may be caused by different ray/visible light converting degree, light/electric converting degree or charge amplifying degree at different pixels. Therefore, in calibration, the X-ray response values may be adjusted to become uniform according to gain parameters at different pixels.

An additional difference between FIG. 2 and FIG. 1 is that the method for calibrating an X-ray detector of the second embodiment may further include the following steps S210, S220.

Step S210: receiving a first calibration image. The above first calibration image is an image generated by directly receiving the X-ray by the above X-ray detector. Directly receiving the X-ray by the X-ray detector means that in the propagation direction of the X-ray, there is no other barrier between a ray source and the X-ray detector, such that, for example, the X-ray detector may receive the X-ray to generate the first calibration image before the X-ray detector has not been installed in any detection device bracket.

Step S220: analyzing the above first calibration image to acquire the above first gain calibration parameter relative to the X-ray detector, and sending the acquired first gain calibration parameter into the X-ray detector for storing. For example, in Step S220, pixel values of individual points of the first calibration image may be acquired and different gain coefficients or gain values are generated for pixel values of individual points respectively in order to allow pixel values of individual points of the first calibration image to be uniform.

Optionally, in order to ensure the evenness of the X-ray received by the X-ray detector, a source image distance (SID) is not less than 180 centimeters when the X-ray detector directly receives said X-ray to produce the above first calibration image.

It can be known from the foregoing description, after the X-ray detector is installed in the detection device bracket, the X-ray will also pass through other barriers before reaching the X-ray detector. In the embodiment of the present invention, due to a material, structure and the like of the barrier, the barrier may also result in unevenness of the X-rays incident to the X-ray detector, thus causing the X-ray detector to have non-uniform (or uneven) pixel response. When a degree of the unevenness resulting from the barrier is small enough to be neglected, calibration may be performed only for the non-uniformity of the pixel response related to the X-ray detector itself. In other words, only the gain calibration parameter related to the X-ray detector itself is retrieved from the X-ray detector and calibration is performed according to the gain calibration parameter. The above first gain calibration parameter is "gain calibration parameter related to the X-ray detector itself".

Figure 3:
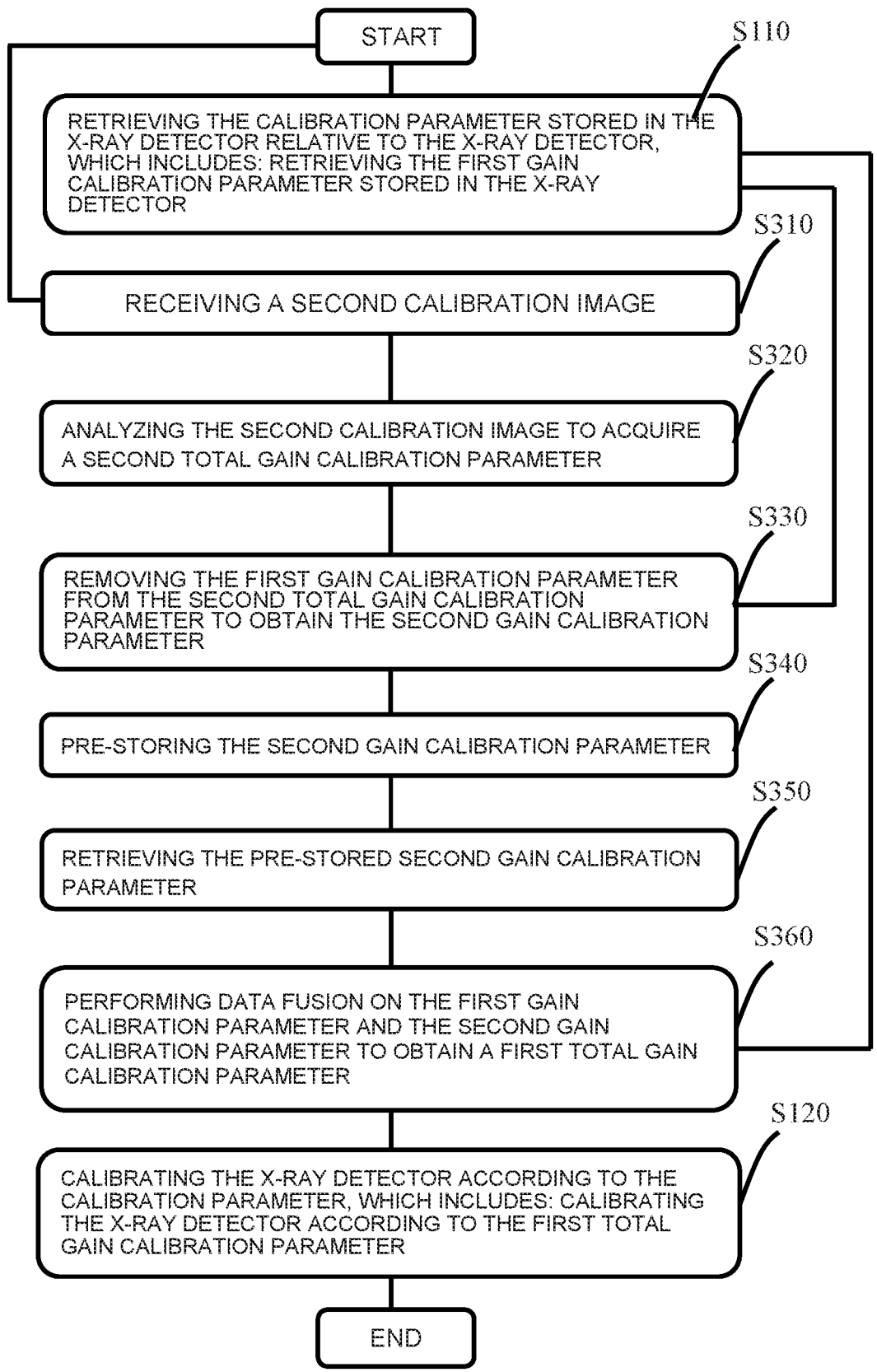
FIG. 3, is a flow chart of a method for calibrating an X-ray detector according to an embodiment of the present invention.

FIG. 3 is a flow chart of a method for calibrating an X-ray detector provided by an embodiment of the present invention. In the present embodiment, in order to calibrate the X-ray detector more accurately such that the unevenness of the pixel response caused by the detection device bracket will not be neglected, in calibration, not only the non-uniformity of the pixel response related to the X-ray detector itself is considered, but also the non-uniformity of the pixel response related to the detection device bracket (the barrier on the detection device bracket) is considered. The third embodiment will be described in details below in conjunction with FIG. 3.

FIG. 3 is similar to FIGS. 1 and 2, and a difference between the embodiments may be: the method for calibrating an X-ray detector in the embodiment depicted in FIG. 3 may further include the following steps S350 and S360 prior to Step S120.

Step S350: retrieving a pre-stored second gain calibration parameter relative to the detection device bracket. Specifically, the second gain calibration parameter relative to the detection device bracket may be pre-stored in a memory of a computer. The computer may be, for example, used for receiving output data of the X-ray detector, controlling an operating parameter of an X-ray bulb, controlling a movement of the detection device bracket, etc. The second gain calibration parameter relative to the detection device bracket may be understood as a gain calibration parameter for calibrating the X-ray detector in order to overcome the unevenness of the X-rays caused by the detection device bracket.

Step S360: performing data fusion on the second gain calibration parameter and the first gain calibration parameter to obtain a first total gain calibration parameter. The above data fusion may include, for example, operations of addition, subtraction, multiplication, division, etc. For example, if the X-ray response values of the pixels need to be multiplied by different gain coefficients to allow the output values of individual pixels to be uniform in calibration, the first gain calibration parameter is multiplied by the second gain calibration parameter to obtain the first total gain calibration parameter in Step S360; if the X-ray response values of individual pixels need to be added with different gain values to allow the output values of individual pixels to be uniform in calibration, the first gain calibration parameter and the second gain calibration parameter are added to obtain the first total gain calibration parameter in Step S360.

Therefore, in the present embodiment, in Step S120, calibrating the X-ray detector according to the calibration parameter may specifically include: calibrating the X-ray detector according to the above first total gain calibration parameter.

Further, depicted in FIG. 3 are the steps of acquiring the above second gain calibration parameter may be also included prior to Step S350, which may specifically include Steps S310, S320, S330 and S340.

Step S310: receiving a second calibration image, which is an image produced by receiving the X-ray by the X-ray detector after the X-ray detector is installed in the detection device bracket.

Step S320: analyzing the second calibration image to acquire a second total gain calibration parameter. At this moment, not only the first gain calibration parameter relative to the X-ray detector, but also the second gain calibration parameter relative to the detection device bracket are included in the second total gain calibration parameter.

Step S330: removing the first gain calibration parameter from the second total gain calibration parameter to obtain the above second gain calibration parameter. For example, the first gain calibration parameter may be subtracted from the second total gain calibration parameter or the second total gain calibration parameter may be divided by the first gain calibration parameter to obtain the second gain calibration parameter.

Step S340: sending the second gain calibration parameter into storage means for pre-storing. For example, in the present step, the second gain calibration parameter may be stored in the memory of the computer.

Figure 4:
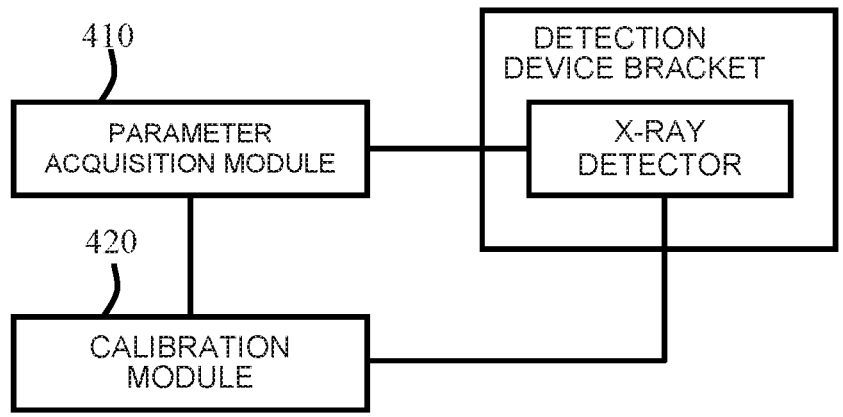
FIG. 4 is a block diagram of an apparatus for calibrating an X-ray detector provided by an embodiment of the present invention.

FIG. 4 is a block diagram of an apparatus for calibrating an X-ray detector provided by an embodiment of the present invention, in which the apparatus may be used for implementing the calibration method as shown in FIG. 1. As shown in FIG. 4, the apparatus may include a parameter acquisition module 410 and a calibration module 420. The parameter acquisition module 410 may be used for retrieving the pre-stored parameter for calibrating the detector from the X-ray detector installed in the detection device bracket. The calibration module 420 may be used for calibrating the X-ray detector according to the above parameter for calibrating the detector.

Optionally, the parameter acquisition module 410 may be used for retrieving the calibration parameter stored in the X-ray detector relative to the X-ray detector.

Optionally, the parameter acquisition module 410 may be used for retrieving the bad pixel calibration parameter stored in the X-ray detector.

Figure 5:
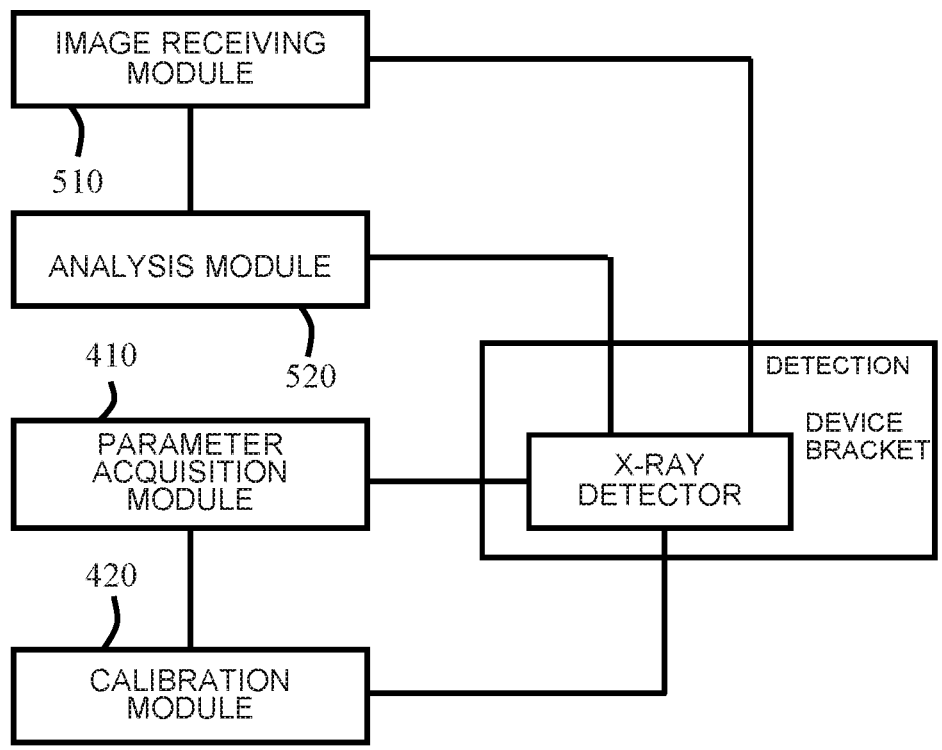
FIG. 5 is a block diagram of an apparatus for calibrating an X-ray detector provided by an embodiment of the present invention.

FIG. 5 is a block diagram of an apparatus for calibrating an X-ray detector provided by an embodiment of the present invention. This apparatus for calibrating an X-ray detector is similar to that of FIG. 4, and a difference between the two may be: the apparatus for calibrating an X-ray detector of FIG. 5 may further include an image receiving module 510 and an analysis module 520. The image receiving module 510 may be used for receiving a first calibration image, which is an image produced by directly receiving the X-ray by the X-ray detector before the X-ray detector is installed in the detection device bracket. The analysis module 520 may be used for analyzing the first calibration image to acquire a first gain calibration parameter relative to the X-ray detector, and sending the acquired first gain calibration parameter into the X-ray detector for storing. Therefore, in the present embodiment, the parameter acquisition module 410 may be specifically used for retrieving the first gain calibration parameter stored in the X-ray detector relative to the X-ray detector.

Figure 6:
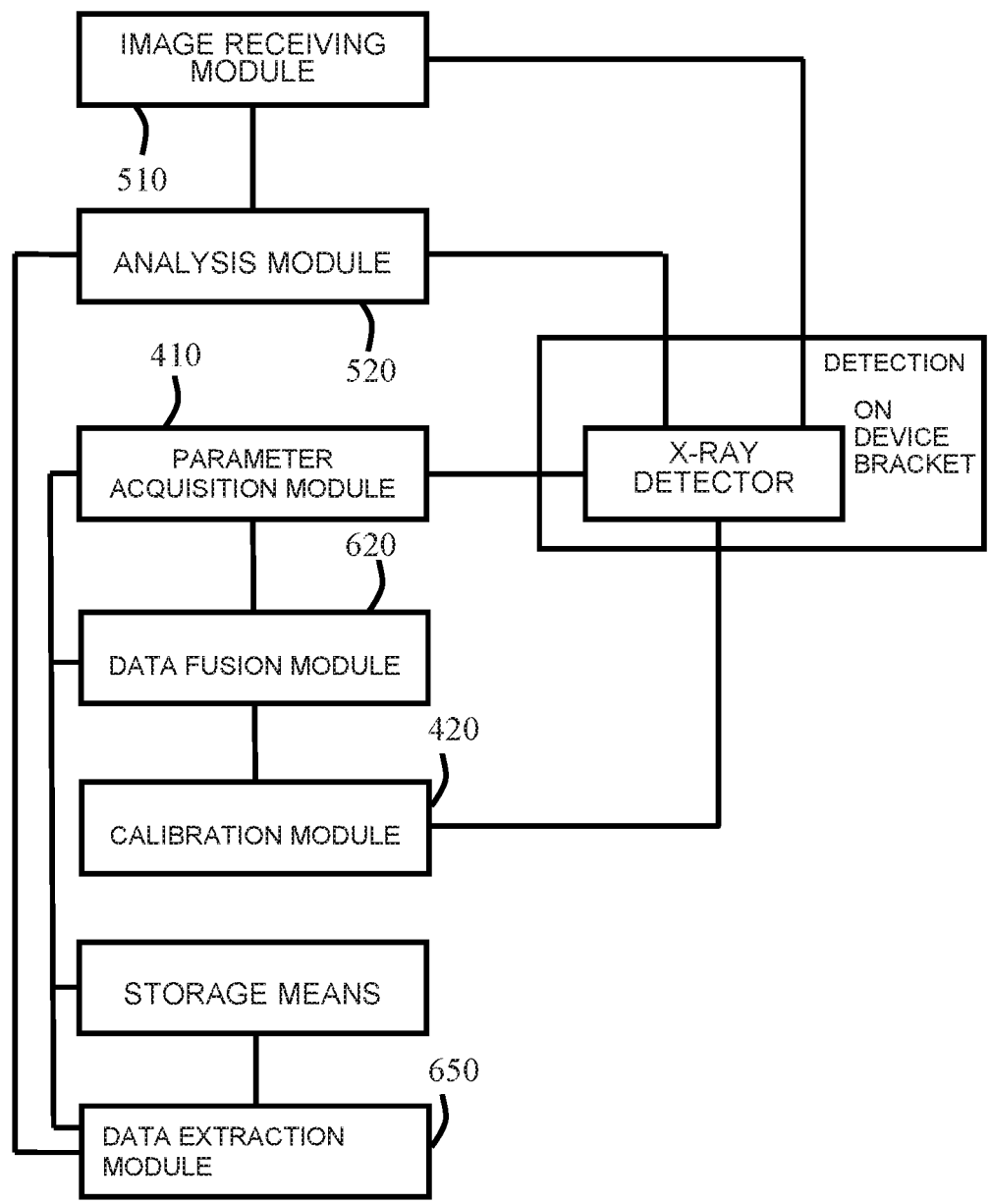
FIG. 6 is a block diagram of an apparatus for calibrating an X-ray detector provided by an embodiment of the present invention.

FIG. 6 is a block diagram of an apparatus for calibrating an X-ray detector provided by an embodiment of the present invention. The apparatus for calibrating an X-ray detector of this embodiment is similar to that of FIGS. 4 and 5, and a difference between the two may be: the parameter acquisition module 410 may further used for retrieving the pre-stored second gain calibration parameter relative to the detection device bracket; and the apparatus for calibrating an X-ray detector of the sixth embodiment may further include a data fusion module 620.

The data fusion module 620 may be used for performing data fusion on the second gain calibration parameter and the first gain calibration parameter to obtain the first total gain calibration parameter. For example, the data fusion module 620 may perform a multiplication operation on the second gain calibration parameter and the first gain calibration parameter to acquire the first total gain calibration parameter. Specifically, the calibration module 420 may calibrate the X-ray detector according to the first total gain calibration parameter.

Optionally, the apparatus for calibrating an X-ray detector of the present embodiment may further include a data extraction module 650. At this moment, the image receiving module 410 may also be used for receiving the second calibration image, which is an image produced by receiving the X-ray by the X-ray detector after the X-ray detector is installed in the detection device bracket. The analysis module 420 may also be used for analyzing the second calibration image to acquire the second total gain calibration parameter. The data extraction module 650 may be used for removing the gain calibration parameter of the X-ray detector from the second total gain calibration parameter to obtain the above second gain calibration parameter, and may be used for pre-storing the obtained second gain calibration parameter, for example, sending the second gain calibration parameter into a memory of a computer for pre-storing.

The operating principle, technical effect and the like of the apparatus for calibrating an X-ray detector of individual embodiments of the present invention are similar to those of the method for calibrating an X-ray detector of the corresponding embodiments, which will not be repeatedly described herein.

Figure 7:
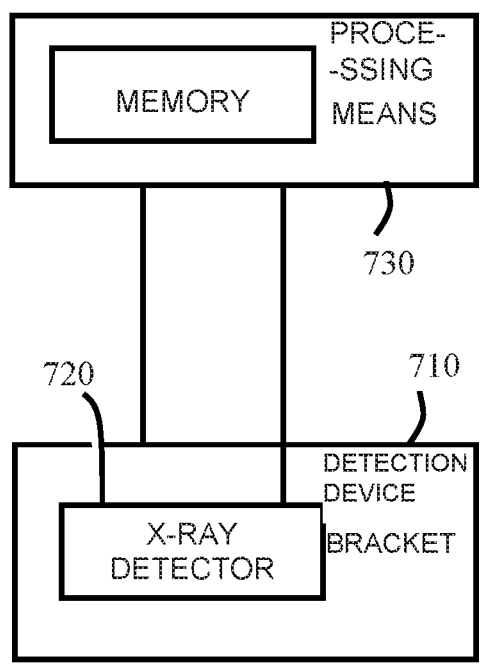
FIG. 7 is a block diagram of an X-ray detection system provided by an embodiment of the present invention.

FIG. 7 is a block diagram of an X-ray detection system provided by a seventh embodiment of the present invention. As shown in FIG. 7, the X-ray detection system includes a detection device bracket 710, an X-ray detector 720, and processing means 730. The X-ray detector 720 may be installed in the detection device bracket 710. The calibration parameter relative to the X-ray detector is stored in the X-ray detector 720.

The processing means 730 may include the apparatus for calibrating an X-ray detector described in the above and shown in FIGS. 4, 5, and 6. The processing means may be, for example, a computer in communication with the detection device bracket 710 and/or the X-ray detector 720. A memory of the computer may be used for pre-storing the second gain calibration parameter relative to the detection device bracket.

In the embodiments of the present invention, the calibration parameter relative to the X-ray is directly stored in the X-ray detector. Accordingly, the calibration parameter may be directly retrieved from the X-ray detector to calibrate the X-ray detector before a patient is scanned. As such, it is not necessary for the detector to receive the X-ray again to produce an original image for calibration and not necessary to regenerate the calibration parameter according to the original image, which avoids repetitive and complicated calibration operations. Moreover, it is not necessary to assign a professional staff to perform the calibration, which improves efficiency. Furthermore, in the embodiments of the present invention, by acquiring the gain calibration parameter relative to the detection device bracket and by performing data fusion on the gain calibration parameter relative to the detection device bracket and the gain calibration parameter relative to the detector in calibration, calibration is performed according to the fused total gain calibration parameter, which thereby may further improve calibration accuracy of the X-ray detector.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other embodiments are also falling within the protection scope of the claims.

What is claimed is:

1. A method for calibrating an X-ray detector, said method for calibrating an X-ray detector comprising:
retrieving a calibration parameter stored in the X-ray detector relative to said X-ray detector, wherein the retrieving of the calibration parameter stored in the X-ray detector relative to said X-ray detector comprises retrieving a first gain calibration parameter stored in said X-ray detector relative to said X-ray detector;
prior to calibrating said X-ray detector, retrieving a pre-stored second gain calibration parameter relative to a detection device bracket that holds said X-ray detector and performing data fusion on said second gain calibration parameter and said first gain calibration parameter to obtain a first total gain calibration parameter; and
calibrating said X-ray detector according to said first total gain calibration parameter.

2. The method for calibrating an X-ray detector according to claim 1, wherein the retrieving of the calibration parameter stored in the X-ray detector relative to said X-ray detector comprises: retrieving a bad pixel calibration parameter stored in said X-ray detector.

3. The method for calibrating an X-ray detector according to claim 1, wherein said method for calibrating the X-ray detector further comprises: receiving a first calibration image, which is an image produced by directly receiving an X-ray by said X-ray detector; and analyzing said first calibration image to acquire said first gain calibration parameter.

4. The method for calibrating an X-ray detector according to claim 3, wherein a source image distance is not less than 180 centimeters when said X-ray detector directly receives said X-ray.

5. The method for calibrating an X-ray detector according to claim 1, wherein the performing data fusion on said second gain calibration parameter and said first gain calibration parameter comprises: multiplying said second gain calibration parameter by a gain calibration parameter of said X-ray detector or adding said second gain calibration parameter to said gain calibration parameter of said X-ray detector.

6. The method for calibrating an X-ray detector according to claim 1, prior to retrieving said pre-stored second gain calibration parameter relative to said detection device bracket, further comprising:
receiving a second calibration image, which is an image produced by receiving an X-ray by said X-ray detector after said X-ray detector is installed in said detection device bracket;
analyzing said second calibration image to acquire a second total gain calibration parameter; removing said first gain calibration parameter from said second total gain calibration parameter to obtain said second gain calibration parameter;
sending said second gain calibration parameter into storage means for pre-storing.

7. An apparatus for calibrating an X-ray detector, said apparatus for calibrating the X-ray detector comprising:
a parameter acquisition module configured to retrieve a calibration parameter stored in the X-ray detector relative to said X-ray detector, wherein said parameter acquisition module is further configured to retrieve a pre-stored second gain calibration parameter relative to a detection device bracket that holds said X-ray detector; and
a calibration module configured to calibrate said X-ray detector, wherein said apparatus for calibrating said X-ray detector comprises a data fusion module configured to perform data fusion on said first gain calibration parameter and said second gain calibration parameter to obtain a first total gain calibration parameter, and wherein the calibration module is configured to calibrate said X-ray detector according to said first total gain calibration parameter.

8. The apparatus for calibrating an X-ray detector according to claim 7, wherein said parameter acquisition module is configured to retrieve a bad pixel calibration parameter stored in said X-ray detector.

9. The apparatus for calibrating an X-ray detector according to claim 7, wherein said apparatus for calibrating said X-ray detector further comprises: an image receiving module configured to receive a first calibration image, which is an image produced by directly receiving an X-ray by said X-ray detector; and an analysis module configured to analyze said first calibration image to acquire said first gain calibration parameter.

10. The apparatus for calibrating an X-ray detector according to claim 9, wherein a source image distance is not less than 180 centimeters when said X-ray detector directly receives said X-ray.

11. The apparatus for calibrating an X-ray detector according to claim 7, wherein said data fusion module is configured to multiply said first gain calibration parameter by said second gain calibration parameter or to add said first gain calibration parameter to said second gain calibration parameter.

12. The apparatus for calibrating an X-ray detector according to claim 7, wherein, said image receiving module is further configured to receive a second calibration image, which is an image produced by receiving an X-ray by said X-ray detector after said X-ray detector is installed in said detection device bracket; said analysis module is further configured to analyze said second calibration image to acquire a second total gain calibration parameter; said apparatus for calibrating said X-ray detector further comprises a data extraction module configured to remove said first gain calibration parameter from said second total gain calibration parameter to obtain said second gain calibration parameter; said data extraction module is further configured to send said second gain calibration parameter into storage means for pre-storing.

13. An X-ray detection device, comprising said detection device bracket and said X-ray detector installed in the detection device bracket, a calibration parameter relative to the X-ray detector being stored in said X-ray detector, said X-ray detection device further comprising processing means, said processing means comprising the apparatus for calibrating said X-ray detector according to claim 7.

14. The method for calibrating an X-ray detector according to claim 1, wherein the detection device bracket comprises a detection bed or supporting pillar.

15. The apparatus for calibrating an X-ray detector according to claim 7, wherein the detection device bracket comprises a detection bed or supporting pillar.

* * * * *